US008603431B2

(12) United States Patent
Ferrini et al.

(10) Patent No.: US 8,603,431 B2
(45) Date of Patent: Dec. 10, 2013

(54) PROCESS FOR PREPARING SILICOALUMINOPHOSPHATE (SAPO) MOLECULAR SIEVES, CATALYSTS CONTAINING SAID SIEVES AND CATALYTIC DEHYDRATION PROCESSES USING SAID CATALYSTS

(75) Inventors: Cristina Ferrini, Breganzona (CH); Daniel Herein, Berlin (DE); David Linke, Berlin (DE); Uwe Rodemerck, Rostock (DE); Evgeny Kondratenko, Rostock (DE)

(73) Assignee: Casale Chemicals S.A. (CH)

( * ) Notice: Subject to any disclaimer, the term of this patent is extended or adjusted under 35 U.S.C. 154(b) by 613 days.

(21) Appl. No.: 12/666,407

(22) PCT Filed: Jun. 30, 2008

(86) PCT No.: PCT/EP2008/005311
§ 371 (c)(1),
(2), (4) Date: Jul. 2, 2010

(87) PCT Pub. No.: WO2009/007031
PCT Pub. Date: Jan. 15, 2009

(65) Prior Publication Data
US 2010/0292071 A1    Nov. 18, 2010

(30) Foreign Application Priority Data

Jul. 6, 2007    (EP) .................................... 07013300

(51) Int. Cl.
*B01J 29/90*    (2006.01)
*B01J 29/06*    (2006.01)

(52) U.S. Cl.
USPC .............................................. 423/700; 502/64

(58) Field of Classification Search
None
See application file for complete search history.

(56) References Cited

U.S. PATENT DOCUMENTS

| 4,440,871 | A | * | 4/1984 | Lok et al. ....................... 502/214 |
| 4,778,780 | A | * | 10/1988 | Valyocsik et al. ............. 502/214 |
| 4,898,722 | A | * | 2/1990 | Derouane et al. ............. 423/701 |
| 5,095,163 | A | * | 3/1992 | Barger ........................... 585/640 |
| 6,914,030 | B2 | * | 7/2005 | Cao et al. ....................... 502/214 |

FOREIGN PATENT DOCUMENTS

| WO | 0074846 A2 | 12/2000 |
| WO | 0125151 A1 | 4/2001 |
| WO | WO 03/035549 | 5/2003 |
| WO | WO 03/057627 | 7/2003 |

\* cited by examiner

*Primary Examiner* — Melvin C Mayes
*Assistant Examiner* — Stefanie Cohen
(74) *Attorney, Agent, or Firm* — Novak, Druce Connolly Bove + Quigg LLP (57) ABSTRACT

A new process for producing a SAPO molecular sieve is disclosed wherein a mixture of a P source with an Al source is subjected to a digestion step under stirring before adding a Si source and a template. The slurry resulting after addition of all chemicals is subjected to a pH adjustment followed by the usual hydrothermal treatment at higher temperature in an autoclave. In this way, very pure highly crystalline SAPO molecular sieves such as SAPO-34 are obtained with a very high yield. In addition, the SAPOs produced this way have an exceptional activity in the dehydration reactions and can be employed as a active component of catalysts for the production of valuable dehydration products from methanol such as, but not limited to, olefins and dimethylether (DME).

21 Claims, 7 Drawing Sheets

—○— S(methane)
--△-- S(ethane)
—○— S(ethylene)
—◇— S(propane)
—●— S(propene)
—+— S(acetylene)
——— S(butane)
—□— S(butenes)
—◇— S(C5 hydrocarbons)
—*— S(coke)
—▲— X(MeOH)

PROCESS FOR PREPARING SILICOALUMINOPHOSPHATE (SAPO) MOLECULAR SIEVES, CATALYSTS CONTAINING SAID SIEVES AND CATALYTIC DEHYDRATION PROCESSES USING SAID CATALYSTS

CROSS-REFERENCE TO RELATED APPLICATIONS

This application is a §371 national stage entry of International Application No. PCT/EP2008/005311, filed Jun. 30, 2008, which claims priority to European Application No. 07013300.4, filed Jul. 6, 2007, both of which are hereby incorporated by reference.

FIELD OF APPLICATION

In its most general aspect, the present invention relates to the production of valuable dehydration products from methanol such as olefins (MTO process) and dimethylether (DME).

In particular, the present invention relates to a process for the production of dehydration products from methanol using a catalyst based on silicoaluminophosphate (SAPO) molecular sieves.

The present invention further relates to a catalyst based on silicoaluminophosphate molecular sieve suitable for use in the production of dehydration products from methanol as well as processes for the preparation of said catalyst and of said sieve, and for the regeneration of said catalyst.

PRIOR ART

The increasing cost of oil has driven the search for alternative processes to produce hydrocarbons from other sources.

Methanol can be obtained from coal or natural gas by the production of synthesis gas. Methanol can be then converted to hydrocarbons by dehydration reactions.

Processes to convert methanol to hydrocarbons are well known. Aluminosilicates or zeolites were used in the beginning as catalysts for this conversion.

Then, it was found that silicolaluminophosphates (SAPOs) can catalyze some dehydration processes involving methanol. For example, EP 1'140'743 discloses a MTO process using a catalyst comprising SAPO-34 as active component. This patent further teaches the importance of the SAPO-34 catalyst synthesis path.

Many workers have experienced that the preparation of SAPOs is highly critical. In particular, the synthesis procedure including the used reactants (Al, Si and P sources and templating agent), the ratios of the elements (Al, Si and P) and template and the observed pH values are determinant to the properties of the resulting materials. Sometimes, it is observed that even using the same reactants different materials may be obtained depending on the synthesis path used, these materials having same chemical composition and SAPO structure as identified by X-ray diffraction but different catalytic properties.

The reaction time for the reactants mixture in the autoclave is also an important parameter in the SAPO-34 synthesis as disclosed in S. H. Jhung, J. S. Chang, J. S. Hwang, S. E. Park, Micro. Meso. Mater., 64 (2003) 33 and J. W. Yoon, S. H. Jung, Y. H. Kim, S. E. Park, J. S. Chang, Bull. Korean. Chem. Soc., 26(4) (2005) 558. In particular, according to these references, for short reaction times the formation of SAPO-5 was observed and it was concluded that SAPO-5 should be a precursor of SAPO-34 formation, so that increasing the reaction time in the autoclave should always lead to pure SAPO-34.

Differently, O. B. Vistad, E. Akporiaye, K. P. Lillerud, J. Phys. Chem. B, 105 (2001) 12437 disclose that the heating rate in the autoclave is a key feature for SAPO synthesis and in this regard only SAPO-5 was observed as crystalline product using fast heating rates in the autoclave.

All these different and partly contradictory statements and observations in SAPO-34 synthesis pathways together with the always different chemicals, templates and element ratios used, pointed out that there seems to be a very complex behaviour between chemicals, element ratios, pH value of the suspension and heating rate in the autoclaves.

Furthermore, according to the prior art, many successful SAPO synthesis procedures require relatively high amounts of template as the teaching is that the presence of the template in excess of the product requirement serves in part to control reaction pH in solution (H. Van Bekkum, E. M. Flanigen, J. C. Jansen, *Studies in Surface Science and Catalysis*, 58 (1991) 142).

In particular, when tetraethylammoniumhydroxide (TEA-OH) is employed as template, a TEA-OH/Al ratio higher than 0.5:1 is generally used. See for instance U.S. Pat. No. 5,126,308 and U.S. Pat. No. 5,912,393.

However, the cost of the reactants to be used for SAPO synthesis is high. In particular, the templates as TEA-OH are known to be very costly. This strongly limits the applicability of the above SAPO-34 synthesis procedures to an industrial level as they require high amounts of reactants.

Attempts have been made to reduce the amount of template utilized in the synthesis by adding a less expensive organic base but this resulted in an increased pressure (organic bases such as dipropylamine are volatile) and would cause environmental and safety concerns. Additionally formation of undesirable dense product is observed. (see U.S. Pat. No. 4,440,871).

Use of polymeric bases as Polyethylenimine was also claimed to be effective in replacing some TEAOH (US2004/0082466 A1) anyhow the attempt to lower the TEAOH/Al ratio below the one indicated above produced a SAPO-34 contaminated with an unidentified phase.

Another drawback of the prior art processes for SAPOs preparation is the formation of unwanted Si—Al islands or domains (zeolitic regions) inside the SAPO that alter the milder acidic character of SAPOs if compared to Si/Al zeolites (see H. Van Bekkum, E. M. Flanigen, P. A. Jacobs, J. C. Jansen, *Studies in Surface Science and Catalysis*, 137 (2001) 378).

In this regard, it should be noted that SAPO materials derive from AlPOs (aluminophosphates) materials that have univariant framework composition Al/P=1. AlPOs are based on framework of $AlO_2^-$ and $PO_2^+$ tetrahedra linked to each other by sharing oxygen atoms. AlPOs are neutral and therefore have nil ion-exchange capacity. When one $SiO_2$ tetrahedra (that has no charge) replaces a $PO_2^+$, then one $AlO_2^-$ bears a now unbalanced negative charge, which will be balanced by an extra framework cation. When the cation is $H^+$ a Broensted acidic side has been created inside the molecular sieve. The fact that Si take a P structure location has been demonstrated for low $SiO_2$ concentrations (see Ashtekar S., Chilukuri S. V. V., Chakrabarty D. K., J. Phys. Chem. 98 (1994) 4878).

SUMMARY OF INVENTION

The technical problem underlying the present invention is then that of providing a process for producing SAPO molecular sieves having high catalytic activity in dehydration reactions which overcomes the prior art drawbacks mentioned above. In particular, the technical problem is that of providing a process for producing SAPO molecular sieves which involves lower costs—so as to be applicable industrially and economically justified—while maintaining both the product purity and the high yield of molecular sieve and through which the formation of Si—Al domains inside the SAPO is hindered.

This problem is solved by a process for producing a SAPO molecular sieve comprising the steps of:
  mixing a P source with an Al source to obtain a mixture,
  adding a Si source and a template to said mixture to obtain a suspension or slurry,
  hydrothermal treating said suspension or slurry to obtain said SAPO molecular sieve suspension,
  recovering said SAPO molecular sieve from said suspension and drying it,
characterized in that said mixture is digested under stirring and heating before adding said Si source and said template.

Preferably, said Al source is chosen between hydrated alumina, preferably pseudoboehmite or aluminium nitrate.

Preferably, said P source is orthophosphoric acid, preferably an aqueous solution thereof, and said Si source is ammonia stabilized silica sol.

Preferably, said template is chosen among aliphatic amines and quaternary ammonium salts, in particular TEA-OH (tetraethyl ammonium hydroxide).

The term "templates" typically refer to structure directing agents that are used to form channels or tunnel-like structures (also called microporous structure) within the molecular sieve composition. For the SAPO materials to be used as catalyst compositions, however, the template must be removed to open up the channels or tunnel-like structures. This is done during the preparation of a SAPO-containing catalyst by calcinating a SAPO-containing powder as it will be better explained here below.

Preferably, appropriate molar ratios of the above reagents (sources) in the final suspension or slurry expressed in terms of P, Al and Si oxides and using TEAOH (tetraethyl ammonium hydroxide) as a templating agent are as follows: $P_2O_5$:$Al_2O_3$:$SiO_2$:TEAOH:$H_2O$=1:(0.8-1.5):(0.1-0.4):(0.6-1.4):(80-130).

More preferably, said molar ratios are as follows: $P_2O_5$:$Al_2O_3$:$SiO_2$:TEAOH:$H_2O$=1:(0.8-1.4):(0.1-0.4):(0.6-1.15):(80-130).

Preferably, the molar ratio of the above reagents is chosen so as to have a Si:Al ratio lower than 0.11 (equivalent to $SiO_2$/$Al_2O_3$=0.22) and a TEAOH:Al ratio lower than 0.5. Preferably, all said reagents have a very low Na content (<0.01%). Silica sol is preferably stabilized with ammonia.

According to the present invention, the digestion step is carried out by stirring the mixture of Al and P sources at a temperature in the range of 50-100° C., preferably 75° C. for a period of time from 10 to 30 hours, preferably 24 hours.

According to an aspect of the present invention, the process may also comprise the step of adjusting the pH of the suspension or slurry obtained by mixing the Si source and the template to the digested mixture. In this regard, the pH is preferably adjusted to slightly acidic conditions, for example 5 to 6.8.

With regard to the hydrothermal treatment step, the final slurry or suspension is closed in a sealed autoclave and heated to 170-220° C., preferably 180-190° C. under stirring. Typically the time varies in the range from about 12 hours to about 80 hours, preferably from about 50 hours to about 72 hours.

The recover of SAPO molecular sieve from the suspension after hydrothermal treatment may be carried out in a conventional way for example by filtration or centrifugation and the recovered SAPO is normally dried.

In contrast to the prior art, applicants have found starting from commercial raw materials and with a very low template content and foreseeing the digestion step of the mixture of Al source (such as alumina) and of P source at a given temperature for a given time followed by the silica and the template addition, final pH adjustment and the usual hydrothermal treatment of the resulting suspension or slurry at higher temperature in an autoclave a very pure highly crystalline SAPO molecular sieve, in particular SAPO-34, is obtained with a very high yield.

Without wishing to be bound to any particular theory, it is believed that the digestion step of the Al source (for example alumina) in the P source (for example an orthophosphoric acid aqueous solution) is essential for the formation of pure SAPO at the lowest template and silica content in the slurry and highest molecular sieve yield. Since the template is the most expensive raw material, one can minimize the synthesis cost.

Moreover the digestion step also allows formation of SAPO with very low silica content. Thus one can tune the acidity since Si substitutes for P in the SAPO synthesis at low silica framework mole fractions, generating consequently a controlled number of the milder acidic sides. (see Barthomeuf D., Zeolites 14 (1994) 394-401 for theoretic aspects).

The critical factor for pure SAPO-34 formation seems to be in fact the formation of a stable and structure directing precursor phase which is obtained, according to the invention, by the digestion step at the given temperature preferably in the range 50 to 100° C., most preferably 75° C.

On the contrary, in contrast to the prior art teachings, the heating rate in the digestion step seems not be critical for pure SAPO-34 formation.

Furthermore, in the process according to the invention, fine tuning of the general Al:P:Si:TEAOH:H2O can be done in the found regimes.

Preferably, in the process according to the invention, the crystals of SAPO material have crystal sizes in the range from 0.2 μm to 5 μm, preferably 1 μm to 3 μm.

The present invention further relates to a SAPO molecular sieve obtainable by the process described above.

This SAPO molecular sieve according to the invention has the following chemical composition:

$$(Si_xAl_yP_z)O_2$$

wherein x, y and z are the mole fraction of Si, Al and P respectively and x is the mole fraction of Si and has a value in the range 0.001-0.1, y is the mole fraction of Al and has a value in the range 0.25-0.5, z is the mole fraction of the P in the range 0.4-0.8.

Preferably, the SAPO molecular sieve is SAPO-34.

Compared to the prior art, the SAPO molecular sieve according to the invention has a low Si/Al molar ratio and also has exceptional catalytic activity in methanol dehydration reactions.

Another aspect of the present invention is then a catalyst comprising a SAPO molecular sieve as above which can be efficiently used in methanol dehydration reactions.

This catalyst may be obtained by a process which comprises the steps of:
  providing a SAPO molecular sieve as described above,
  mixing or inserting said SAPO molecular sieve with/in a matrix/binder material to obtain a paste or suspension,
  treating said paste or suspension to obtain solid particles,
  calcinating said solid particles to obtain said catalyst.

The above process may further comprises the step of calcinating said SAPO molecular sieve before mixing or inserting it with/in a matrix/binder material.

In this process, the matrix material acts as a diluent but also as a continuous binder phase between the molecular sieve crystallites to form a paste or suspension. This paste is then treated to form solid particles by extrusion, compression techniques or atomisation to form extrudates, pellets or microspheres and these solid particles are subjected to a calcination procedure.

Preferably, the paste contains 40-98% by weight (on dry basis) of matrix material and 2-60% by weight (on dry basis) of molecular sieve. Most preferably, when catalyst is used for DME, 70-98% by weight of matrix material and 2-30% by weight of molecular sieve, when catalyst is used for MTO, 40-70% by weight of matrix material and 60-30% by weight of molecular sieve.

Suitable matrix material that does not affect the catalytic properties of the molecular sieve are activated alumina, silica, aluminium silicate, silica-alumina and natural caoline. Preferably, said matrix materials have a high surface area and good binding properties given from reactive surface groups.

Preferred matrix materials consist for DME of activated aluminas having at least 50% by weight of pseudoboehmite, of silica and silica-alumina for MTO.

Preferably, said solid particles are in the form of pellets, tablets, extrudates or microspheres.

According to an aspect of the present invention, the calcination of the mixture of molecular sieve and matrix material and optionally of molecular sieve alone is carried out at temperatures not exceeding 600° C. Preferably, said calcination is started at ambient temperature and the temperature is gradually increased in 4-10 hours and in one or more steps up to the desired temperature and kept at this temperature for further 4-8 hours.

According to a preferred aspect of the present invention, said calcination is carried out in presence of an inert gas as argon or nitrogen up to 500° C.

In this way, it has been surprisingly found that the calcination's procedure is shorter and can be achieved at lower temperatures while at the same time the inert gas acts a sort of stripping agent that allows the template to be removed in a substantially complete way. Furthermore, the catalyst so obtained shows a higher resistance and lifetime during its use in methanol dehydration reactions such as the conversion of methanol to DME or olefins.

According to another aspect of the present invention, the catalyst is in the form of pellets or extrudates having 1-6 mm diameter and 1-5 mm length.

According to a further aspect of the present invention, the catalyst is in the form of microspheres having medium diameter form 0.05 to 0.08 mm.

The present invention also relates to a process for dehydrating methanol to valuable chemicals as olefins and DME, which comprises the step of contacting methanol with a catalyst as described above under conditions effective to convert methanol to one of said chemicals.

The process for converting methanol to dehydration products as olefins or DME may be performed in a reactor having a fixed bed or a fluidized bed of said catalyst. The reactor may be isothermal with cooling surfaces in direct contact with the shaped catalyst or adiabatic with a plurality of catalytic beds and intercooling between the beds.

The operating conditions are to be optimized for the selected dehydration. Milder conditions, i.e. temperatures in the range between 150 to 250° C. will lead to the selective formation of DME, higher temperatures (higher than 250° C.) lead to olefines.

Preferably, the operating pressure in the reactor is in the range from atmospheric pressure to 20 bar, preferably 5 to bar and the methanol flow has a space velocity, expressed as liters of liquid methanol supplied per hour for liters of catalyst volume, in the range of 1 to 50 $h^{-1}$, preferably 1 to 5 $h^{-1}$.

In an embodiment of the present invention, the reaction products are fed as vapour streams to the fractionation columns.

The present invention further relates to processes for regenerating the catalytic activity of a catalyst as described above. After each cycle of its use in a process according to the invention for converting methanol to DME or olefins, the regenerating process comprising the step of passing across the catalyst at least one flow of a regenerating agent chosen among nitrogen, argon, hydrogen, air, steam and mixtures thereof at a temperature of maximum 550° C. for a period from 1 to 12 hours.

In a process for converting methanol to olefins the regeneration is done in the regenerator with continuous circulation of the coked catalyst from reactor to regenerator. The air is injected to the dense bed of catalyst in the regenerator. By steam or nitrogen purging in the risers, the catalyst is purified by the methanol and hydrocarbons adsorbed in reactor and oxygen adsorbed in regenerator.

Further characteristics and advantages of the present invention will be more evident from the examples provided here below, given as indicative and not limiting purpose with reference to the annexed drawings.

EXAMPLE 1

Synthesis of Pure SAPO-34 Molecular Sieve 100 g $H_2O$ and 15.6 g $H_3PO_4$ (85%) were mixed at 25° C. 11.2 g of pseudo-boehmite ($AlOOH.H_2O$ equivalent to 65.4% $Al_2O_3$) were added slowly at 25° C. under stirring. This suspension was heated to 75° C. and stirred for additional 24 h. After this time period 3.6 g $SiO_2$-sol (25%) and 40.7 g TEAOH solution (25%) were added at 75° C. under stirring. Immediately after the final addition of the Si— and Template sources the pH value was adjusted with conc. $HNO_3$ (~3 ml) to 6.8 at 75° C. The resulting final suspension was heated for 3 days at 185° C. in an autoclave, filtered, washed with $H_2O$ and dried at 110° C. for 12 h. Yield after drying 20 g (~80% of the theoretical yield).

Details of the total element and template amounts and ratios are given in Table 1.

Figure 1:
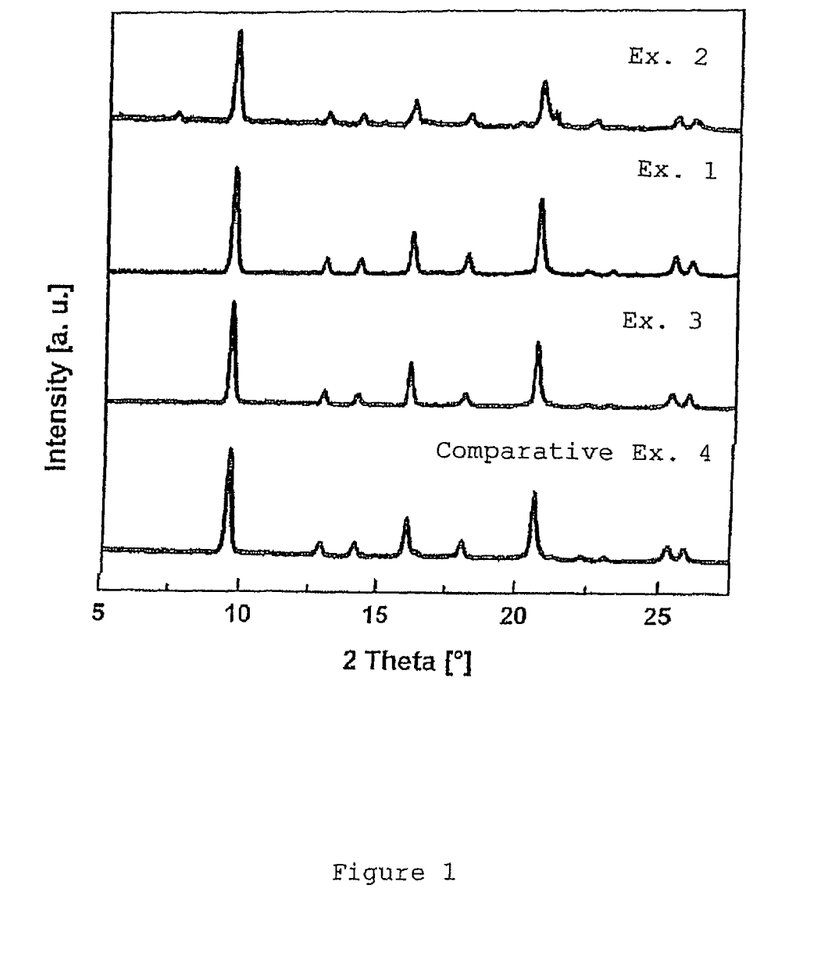
FIG. 1 shows the X-ray diffraction pattern of SAPO-34 materials according to the invention obtained through the procedures disclosed in the examples 1-3 here below and of SAPO-34 material obtained through the procedure disclosed in comparative example 4 here below.
Figure 2:
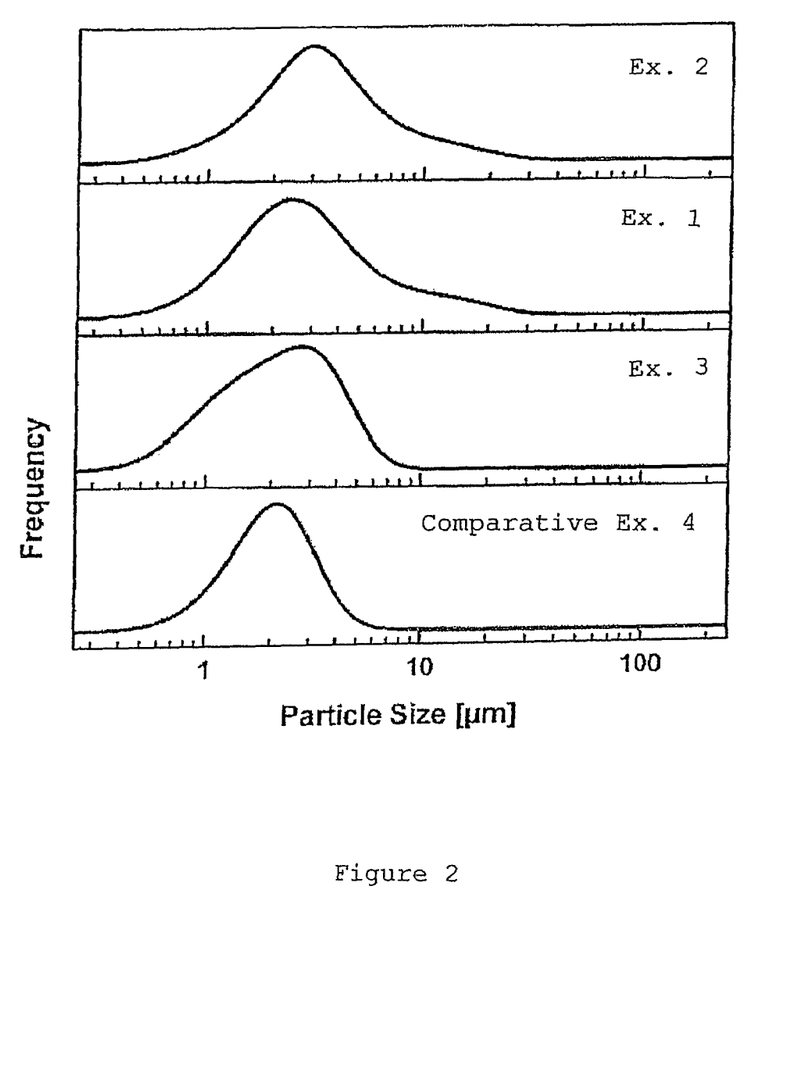
FIG. 2 shows the particle size distribution of the SAPO-34 materials of FIG. 1.

The X-ray diffraction pattern showing a pure SAPO-34 phase is given in FIG. 1. The particle size distribution is given in FIG. 2.

EXAMPLE 2

Synthesis of Pure SAPO-34 Molecular Sieve

The synthesis was carried out identical to the described synthesis recipe of example 1. The pH was adjusted with ~3 ml $H_3PO_4$ (85%). The yield after drying was 20 g (~80% of the theoretical yield). Details of the total element and template amounts and ratios are given in Table 1.

TABLE 1

Amounts and ratios used for the syntheses of examples 1 and 2.

| Ex. No. | | H2O | AlOOHx H2O | H3PO4 (85%) | H2O | Temp. | Time | pH | SiO2 (25%) | H2O | TEAOH (25%) | H2O | Sum H2O |
|---|---|---|---|---|---|---|---|---|---|---|---|---|---|
| 1 | Gram | 100.0 | 11.20 | 15.60 | 2.30 | | | | 3.60 | 2.70 | 40.70 | 30.5 | 135.5 |
|   | Mol | 5.56 | 0.1435 | 0.135 | 0.13 | 75 | 24 | 2.60 | 0.015 | 0.15 | 0.069 | 1.7 | 7.54 |
|   | Ratio* | | 1.06 | 1.00 | | | | | 0.11 | | 0.49 | | 53.8 |
| 2 | Gram | 100.0 | 11.20 | 20.65 | 3.06 | | | | 3.60 | 2.70 | 40.70 | 30.5 | 136.3 |
|   | Mol | 5.56 | 0.1435 | 0.179 | 0.17 | 75 | 24 | 2.60 | 0.015 | 0.15 | 0.069 | 1.7 | 7.58 |
|   | Ratio* | | 0.80 | 1.00 | | | | | 0.084 | | 0.385 | | 42.3 |

*equivalent to
for Ex. 1: $P_2O_5:Al_2O_3:SiO_2:TEAOH:H_2O = 1:1.06:0.22:0.98:107.6$
for Ex. 2: $P_2O_5:Al_2O_3:SiO_2:TEAOH:H_2O = 1:0.8:0.17:0.77:84.6$ Note:
the total amounts of $H_3PO_4$, $SiO_2$-sol and TEAOH solution in gram include the separately listed $H_2O$ content of these chemicals (which is only listed to calculate the overall $H_2O$ amount used in the synthesis recipe).

The X-ray diffraction pattern showing a pure SAPO-34 phase is given in FIG. 1. The particle size distribution is given in FIG. 2.

EXAMPLE 3

Synthesis of Pure SAPO-34 Molecular Sieve 100 g $H_2O$ and 11.2 g $H_3PO_4$ (85%) were mixed at 25° C. 11.2 g of pseudo-boehmite were added slowly at 25° C. under stirring. This suspension was heated to 75° C. and stirred for additional 24 h. After this time period 3.6 g $SiO_2$-sol 25% and 40.7 g TEAOH solution (25%) were added at 75° C. under stirring. Immediately after the final addition of the Si— and Template sources the pH value was adjusted with conc. $HNO_3$ (~4 ml) to 6.8 at 75° C. The resulting final suspension was heated for 3 days at 185° C. in an autoclave, filtered, washed with $H_2O$ and dried at 110° C. for 12 h. Yield after drying 14 g (~56% of the theoretical yield).

Details of the total element and template amounts and ratios are given in Table 1.

TABLE 2

Amounts and ratios used for the syntheses of example 3.

| No. | | H2O | AlOOHx H2O | H3PO4 (85%) | H2O | Temp. | Time | pH | SiO2 (25%) | H2O | TEAOH (25%) | H2O | Sum H2O |
|---|---|---|---|---|---|---|---|---|---|---|---|---|---|
| 1 | Gram | 100.0 | 11.20 | 11.2 | 1.7 | | | | 3.60 | 2.70 | 40.70 | 30.5 | 135.5 |
|   | Mol | 5.56 | 0.1435 | 0.097 | 0.09 | 75 | 24 | 4.20 | 0.015 | 0.15 | 0.069 | 1.7 | 7.5 |
|   | Ratio | | 1.48 | 1.00 | | | | | 0.15 | | 0.7 | | 53.8 |

*equivalent to $P_2O_5:Al_2O_3:SiO_2:TEAOH:H_2O = 1:1.48:0.3:1.4:107.6$

Note:
the total amounts of $H_3PO_4$, $SiO_2$-sol and TEAOH solution in gram include the separately listed $H_2O$ content of these chemicals (which is only listed to calculate the overall $H_2O$ amount used in the synthesis recipe).

The X-ray diffraction pattern showing a pure SAPO-34 phase is given in FIG. 1. The particle size distribution is given in FIG. 2.

EXAMPLE 4 (COMPARATIVE EXAMPLE)

Synthesis of SAPO-34 Molecular Sieve 50 g $H_2O$ and 15.6 g $H_3PO_4$ 85% were mixed at 25° C. 11.2 g of pseudo-boehmite were added slowly at 25° C. under and stirred for additional 24 h at 25° C. After this time period 3.6 g $SiO_2$-sol 25% were added under stirring. The pH of the suspension was adjusted to 6.8 using the addition 72 g TEAOH solution and 25 g $H_2O$ at 25° C. under stirring. The resulting final suspension was heated for 3 days at 185° C. in an autoclave, filtered, washed with $H_2O$ and dried at 110° C. for 12 h. Yield after drying 11 g (~44% of the theoretical yield).

Using a higher amount of TEA-OH premixing all chemical at 25° C. led to pure SAPO-34 material with, however, lower yields.

Details of the total element and template amounts and ratios are given in Table 3.

TABLE 3

Amounts and ratios used for the syntheses of example 4.

| No. | | H2O | AlOOHx H2O | H3PO4 (85%) | H2O | Temp. | Time | pH | SiO2 (25%) | H2O | TEAOH (25%) | H2O | H2O | Sum H2O |
|---|---|---|---|---|---|---|---|---|---|---|---|---|---|---|
| 1 | Gram | 50.0 | 11.20 | 15.6 | 2.3 | | | | 3.60 | 2.70 | 72.00 | 54.0 | 25.0 | 134 |
| | Mol | 2.78 | 0.135 | 0.1435 | 0.13 | 25 | 24 | 2.40 | 0.015 | 0.15 | 0.12 | 3.00 | 1.39 | 7.44 |
| | Ratio | | | 1.06 | 1.00 | | | | 0.11 | | 0.90 | | | 55.02 |

*equivalent to $P_2O_5:Al_2O_3:SiO_2:TEAOH:H_2O = 1:1.06:0.22:1.8:110.04$
Note:
the total amounts of $H_3PO_4$, $SiO_2$-sol and TEAOH solution in gram include the separately listed $H_2O$ content of these chemicals (which is only listed to calculate the overall $H_2O$ amount used in the synthesis recipe).

The X-ray diffraction pattern showing a pure SAPO-34 phase is given in FIG. 1. The particle size distribution is given in FIG. 2.

EXAMPLE 5 (COMPARATIVE EXAMPLE)

Synthesis of SAPO-34 Molecular Sieve

Several syntheses were carried out with elements and template ratios identical to those of the synthesis recipe of example 1 without the stirring and heating step after the mixing of the phosphate and alumina sources. Any possible addition sequence was tested. Different autoclave synthesis times between 2-7 days and heating rates led to non-successful SAPO-34 synthesis. Non-successful in this connection means that the product materials always consisted of pure SAPO-5 or mixture of SAPO-5 and SAPO-34 in various ratios.

EXAMPLE 6

Catalyst Formulation 140 g of SAPO powder as synthesized obtained according to the procedure given in example 1 or 2 (containing 100 g of dry matter, the balance being humidity) are mixed with 800 g of ammonia-stabilized colloidal silica at 8.5% $SiO_2$. The suspension is stirred till it is homogeneous. The slurry is maintained under stirring and is atomised by spray drying in the following conditions:
  inlet air temperature: 420° C.
  outlet air temperature: 150° C.
  injection pressure 4 bar
The product is then submitted to calcination in air at 550° C. for 10 hours. In a first period the temperature is raised to 350° C. in 6 hours, and kept at this level for 2 hours, in a second period the temperature is raised to 550° C. with a heating rate of 2° C./min and kept for 10 hours. The weight loss during calcination is about 30% of the initial weight. The final product is composed by spheres of an average particle size of 50-80 μm.

EXAMPLE 7

Calcination Procedure

A molecular sieve for a catalyst according to the invention was prepared according to the procedure of example 1. The calcination was carried out in the presence of air or of an inert gas (argon) at a temperature up to 500° C. It was surprisingly found that the calcination in inert gas is more efficient in removing completely the template at milder conditions.

Figure 5:
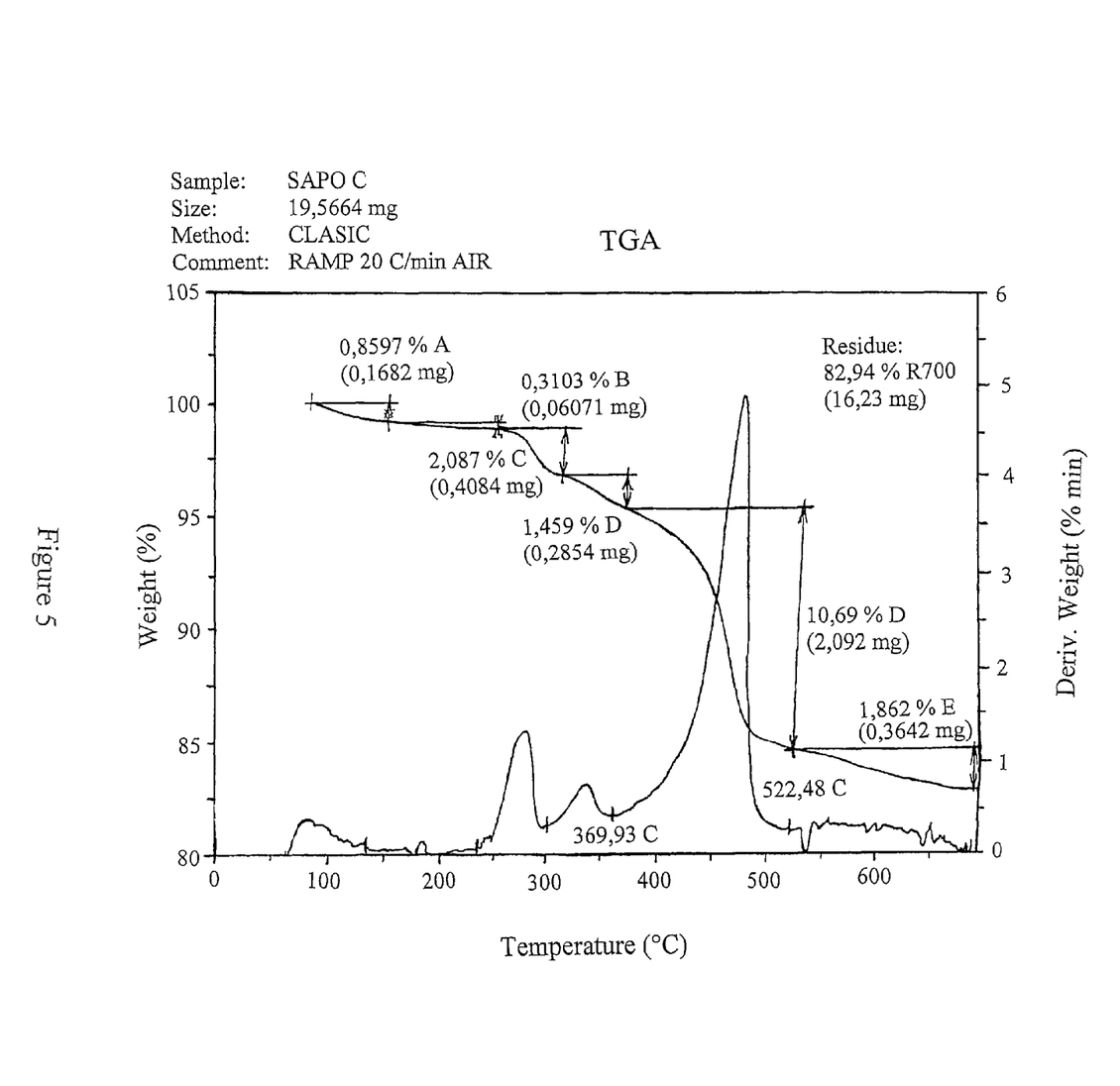
FIG. 5 shows the thermogravimetric analysis of the as-synthesized SAPO-34 molecular sieve according to the invention in air.
Figure 6:
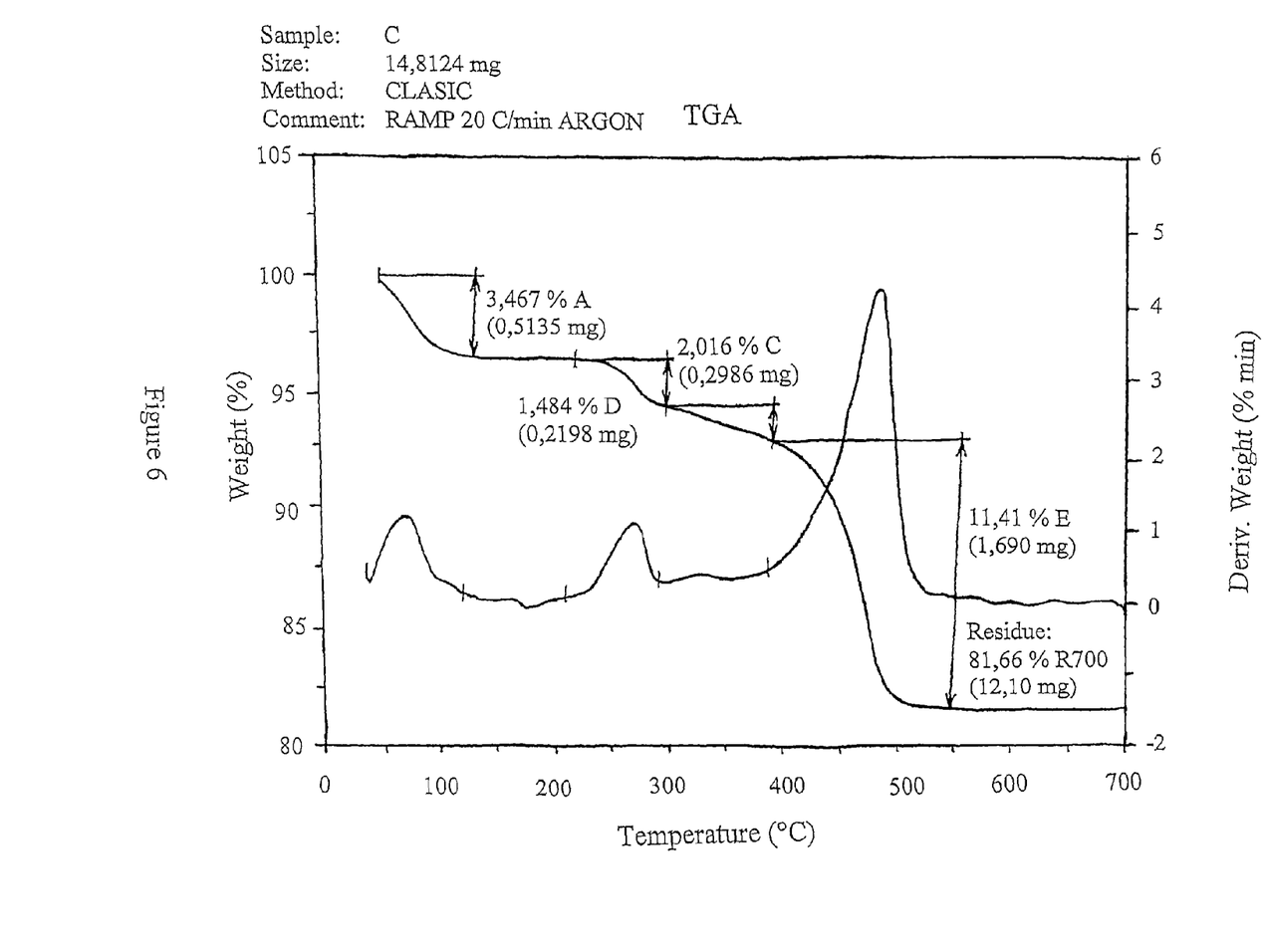
FIG. 6 shows the thermogravimetric analysis of the as-synthesized SAPO-34 molecular sieve according to the invention in argon.
Figure 7:
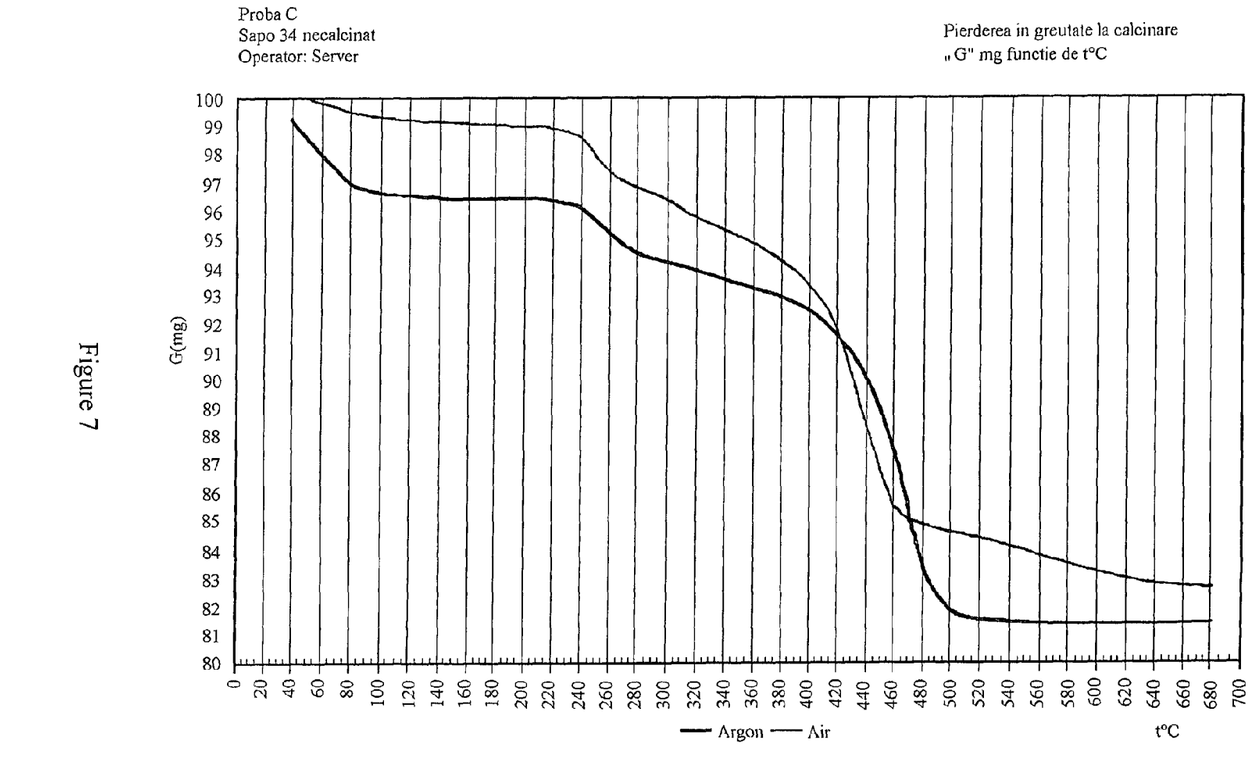
FIG. 7 shows a superposition of the thermogravimetric analysis of FIGS. 5 and 6 of the as-synthesized SAPO-34 molecular sieve in air and in argon respectively.

As can be seen in FIG. 5, the thermal analysis of as synthesised molecular sieve sample obtained according to example 1 in air shows continuous weight loss after 550° C. till 700° C. Thermogravimetric curves made in inert medium, Argon of the molecular sieve according to this example (FIG. 6) exhibit total organic material removing at 550° C. The superposition of the weight loss curves in FIG. 7 shows more clearly these differences.

EXAMPLE 8

Catalytic Results of SAPO-34 Molecular Sieves in the MTO Reaction 300 mg of each catalyst synthesized according to Example 6 containing SAPO-34 according to the example 1 or 2 were tested in the MTO reaction. The catalyst samples were tested at four reaction conditions:

T=480° C., GHSV=3.4 h$^{-1}$

T=480° C., GHSV=2.1 h$^{-1}$

T=420° C., GHSV=2.1 h$^{-1}$

T=420° C., GHSV=1.7 h$^{-1}$

The feed was composed of methanol (80 vol %) and nitrogen (20 vol %). At all of the above reaction conditions all catalysts are tested for 90 minutes each. After this the catalysts were regenerated in air flow at 550° C. for 60 minutes. Then, a second test at the same reaction conditions followed to check if the catalysts reach their full activity after regeneration. After a second regeneration the test at the next reaction condition followed and so on. Altogether, each of the catalyst samples has been tested and regenerated 8 times without loss in activity.

Figure 3:
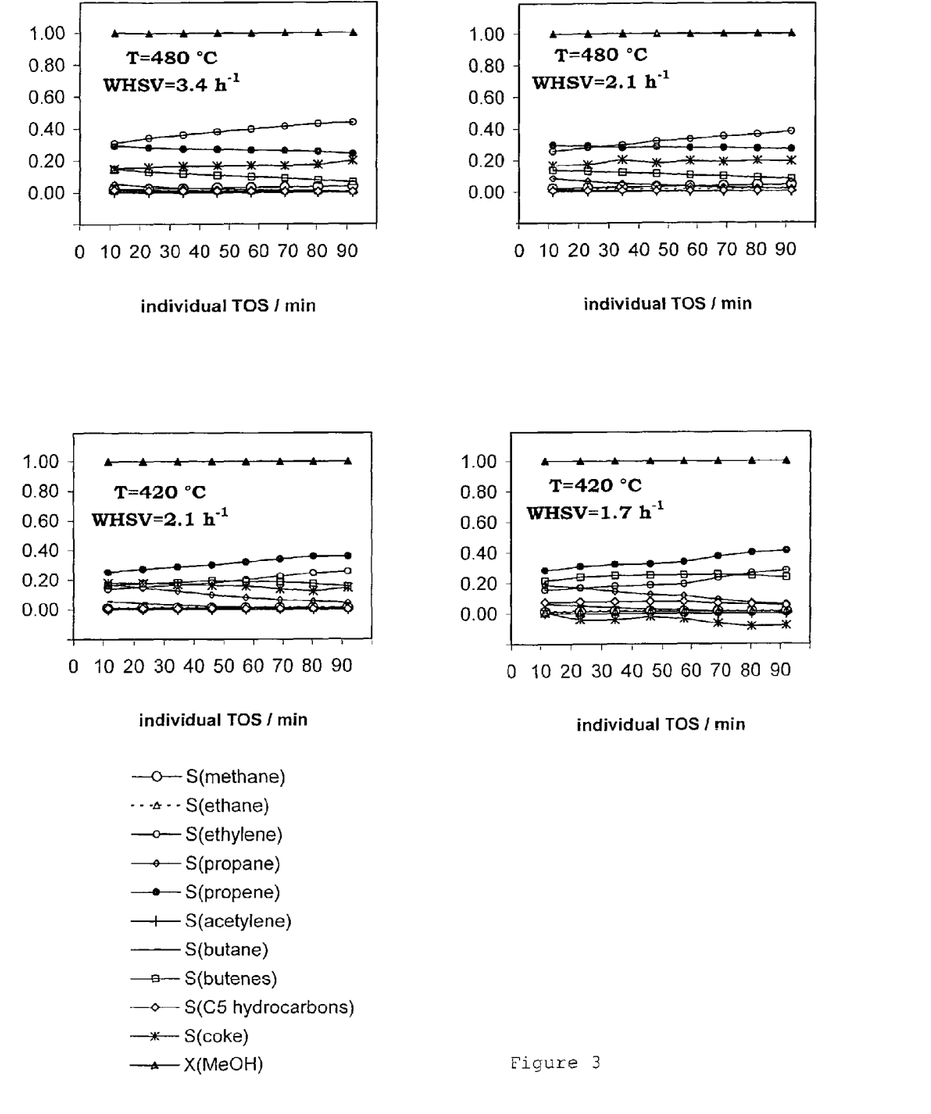
FIG. 3 shows the catalytic results for a catalyst comprising the SAPO-34 of the invention obtained according to the example 1 here below.
Figure 4:
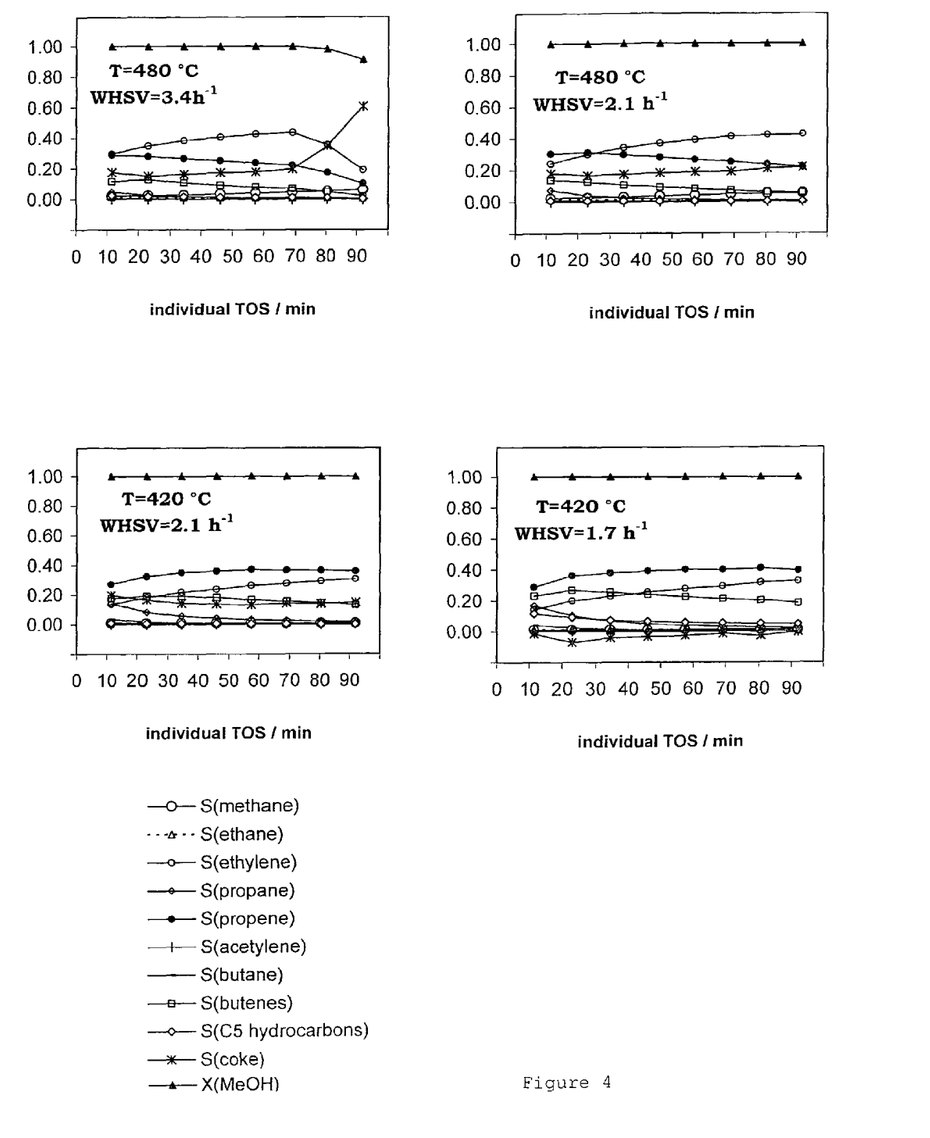
FIG. 4 shows the catalytic results for a catalyst comprising the SAPO-34 of the invention obtained according to the example 2 here below.

Results are given in FIG. 3 for the catalyst comprising SAPO-34 according to the example 1 and in FIG. 4 for the catalyst comprising SAPO-34 according to the example 2.

At the reaction conditions applied the methanol conversion is 100%. Practically no deactivation was detected after the reaction time for both samples of catalyst started showing deactivation after 70 minutes at higher temperature.

In general, the main reaction products are propene and ethylene followed by butenes, propane and butane. Methane, ethane, acetylene and C5 hydrocarbons are detected only in traces.

The product selectivities as well as the ratios between the different hydrocarbons are mainly influenced by reaction temperature.

At 480° C. ethylene is the main reaction product whereas at the lower reaction temperature 420° C. the selectivity of propene is higher. Also more butanes and propane are formed at 420° C. compared to the higher temperature. At both temperatures propane and butene selectivity decrease with time whereas propene formation is enhanced. The selectivity of methane, ethane, acetylene and the C5 hydrocarbons is generally low.

Coke formation is displayed as its selectivity as calculated from the carbon balance.

EXAMPLE 9

Shaping of Catalyst and Catalytic Results of SAPO-34 Molecular Sieves in the DME Reaction 10 g of dried uncalcined SAPO-34 synthesized according to the procedure of example 1 were mixed with 51.5 g hydrated alumina. To this mixture, 30 g diluted nitric acid (10%) was added. The homogeneous paste obtained was extruded using a 2 mm diameter nozzle. The extrudates were dried at 100° C. and subsequently calcined in air. The temperature was increased from room temperature to 600° C. in 6 hours and maintained at this temperature for 8 hours.

ml catalyst were tested in an electrically heated reactor at different temperatures and pressures. Space velocity used was LHSV=1 h$^{-1}$ (liters liquid methanol/liters catalyst.hours). After cooling and condensation liquid products were analysed, uncondensed gaseous product were conducted to a gas chromatograph. The results obtained are presented in Table 4.

TABLE 4

| Pres. atm | atm | atm | 9.7 | 10 |
|---|---|---|---|---|
| Temp. ° C. | 178 | 203 | 176 | 208 |
| Gaseous product analysis wt % | | | | |
| Methane + ethane | | 0.03 | 0.02 | 0.14 |
| propane | | | | 0.01 |
| propylene | 0.04 | 0.04 | 0.04 | 0.05 |
| butanes | | 0.01 | | |
| butenes | | | | |
| dimethylether | 99.72 | 99.76 | 99.75 | 99.71 |
| C5+ | 0.23 | 0.16 | 0.19 | 0.16 |
| Liquid products analysis wt % | | | | |
| dimethylether | 6.71 | 3.63 | 7.04 | 4.42 |
| Methanol | 55.75 | 34.51 | 71.16 | 77.42 |
| water | 37.54 | 61.26 | 21.8 | 18.16 |
| Methanol conversion | 70.5 | 86.4 | 52.1 | 45.5 |

The invention claimed is:

1. Process for producing a SAPO molecular sieve having a SAPO-34 crystal structure, the process comprising the steps of:
mixing a P source with an Al source to obtain a mixture,
adding a Si source and a template to said first mixture to obtain a suspension or slurry,
optionally adjusting the pH of said slurry or suspension to a value in the range from 5 to 6.8,
hydrothermal treating said suspension or slurry to obtain said SAPO molecular sieve suspension,
recovering said SAPO molecular sieve from said suspension and drying it, characterized in that said mixture of Al and P sources is digested under stirring before adding said Si source and said template, said digestion step being carried out at a temperature in the range of 50-100° C. for a period of time from 10 to 30 hours.

2. Process according to claim 1, characterized in that said Al source is chosen between hydrated alumina, preferably pseudobohemite or aluminium nitrate, said P source is ortho-phosphoric acid, said Si source is silica sol preferably ammonia stabilized, and said template is chosen among aliphatic amines and quaternary ammonium salts.

3. Process according to claim 2, characterized in that said template is TEAOH (tetraethyl ammonium hydroxide) and said slurry or suspension has the following molar composition, expressed as P, Al and Si oxides: $P_2O_5:Al_2O_3:SiO_2$: $TEAOH:H_2O=1:(0.8-1.5):(0.1-0.4):(0.6-1.4):(80-130)$.

4. Process according to claim 3, characterized in that said slurry or suspension has a Si:Al ratio lower than 0.11 (equivalent to $SiO_2/Al_2O_3$ lower than 0.22) and a TEAOH:Al ratio lower than 0.5 (equivalent to $TEAOH/Al_2O_3$ lower than 1).

5. The process according to claim 3, wherein said slurry or suspension has the following molar composition, expressed as P, Al and Si oxides: $P_2O_5:Al_2O_3:SiO_2:TEAOH:H_2O=1:$ $(0.8-1.4):(0.1-0.4):(0.6-1.15):(80-130)$.

6. The process according to claim 2, wherein said template is TEA-OH.

7. Process according to claim 1, characterized in that said hydrothermal treatment step of said slurry or suspension is carried out at a temperature in the range of 170-220° C. under stifling, for a time in the range from about 12 hours to about 80 hours.

8. The process according to claim 7, wherein said hydrothermal treatment step of said slurry or suspension is carried out at a temperature in the range of 180-190° C. under stirring, for a time in the range from about 50 hours to about 72 hours.

9. The process according to claim 1, wherein said digestion step is carried out at a temperature of 75° C. for 24 hours.

10. SAPO molecular sieve having a SAPO-34 crystal structure, and characterized in that it is obtainable by a process according to claim 1 and has the following chemical composition:

$$(Si_xAl_yP_z)O_2$$

wherein x, y and z are the mole fraction of Si, Al and P respectively and x is the mole fraction of Si and has a value in the range 0.001-0.1, y is the mole fraction of Al and has a value in the range 0.25-0.5, z is the mole fraction of the P in the range 0.4-0.8.

11. Catalyst comprising a SAPO molecular sieve according to claim 10 and a matrix material selected from the group comprising alumina, silica, aluminium silicate, silica-alumina, natural caoline, and activated alumina having at least 50% by weight of pseudoboehmite.

12. Catalyst according to claim 11, characterized in that it comprises 40-98% by weight of said matrix and 2-60% by weight of said SAPO molecular sieve, preferably, when catalyst is used for DME, 70-98% by weight of matrix material and 2-30% by weight of molecular sieve and when catalyst is used for MTO, 40-70% by weight of matrix material and 60-30% by weight of molecular sieve.

13. Catalyst according to claim 11, characterized in that it is in the form of pellet or extrudates having 1-6 mm diameter and 1-5 mm length or in the form of microspheres having medium diameter from 0.05 to 0.08 mm.

14. Process for preparing a catalyst according to claim 11, characterized in that it comprises the steps of:
providing a SAPO molecular sieve according to claim 10,
mixing or inserting said SAPO molecular sieve with/in a matrix material to obtain a paste or suspension,
treating said paste or suspension to obtain solid particles, and
calcinating said solid particles to obtain said catalyst.

15. Process according to claim 14, characterized in that said calcination is carried out at temperatures up to 600° C.

16. Process according to claim 15, characterized in that said calcination is carried out in an inert gas up to 500° C.

17. The process according to claim 16, wherein said calcination is carried out in argon or nitrogen up to 500° C.

18. The process according to claim 15, wherein said calcination is carried out at temperatures starting at ambient temperature and gradually increasing the temperature in 4-10 hours up to 600° C. and maintaining the temperature at 600° C. for a further 4-8 hours.

19. Process for converting methanol to DME characterized in that it comprises the step of contacting methanol with a catalyst according to claim 11 under conditions effective to convert methanol to DME.

20. Process for converting methanol to olefins characterized in that it comprises the step of contacting methanol with a catalyst according to claim 11 under conditions effective to convert methanol to olefins.

21. Process for regenerating the catalytic activity of a catalyst according to claim 11 after a cycle of its use in a process for converting methanol to DME or olefins, the regenerating process comprising the step of passing across the catalyst at least one flow of a regenerating agent chosen among nitrogen, argon, hydrogen, air, steam and mixtures thereof at a temperature of maximum 550° C. for a period from 1 to 12 hours.

* * * * *